(12) United States Patent
Christiansen et al.

(10) Patent No.: US 8,460,360 B2
(45) Date of Patent: *Jun. 11, 2013

(54) PROSTHESIS COUPLING DEVICE AND METHOD

(75) Inventors: Frank K. Christiansen, Haslev (DK); Krasnodar Ivancev, Camden (GB)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/609,925

(22) Filed: Sep. 11, 2012

(65) Prior Publication Data

US 2013/0013052 A1 Jan. 10, 2013

Related U.S. Application Data

(62) Division of application No. 12/867,101, filed as application No. PCT/US2009/000869 on Feb. 11, 2009, now Pat. No. 8,277,499.

(60) Provisional application No. 61/065,333, filed on Feb. 11, 2008.

(51) Int. Cl.
*A61F 2/06* (2006.01)

(52) U.S. Cl.
USPC ............................... 623/1.13; 606/151

(58) Field of Classification Search
USPC ............ 623/1.12, 1.13, 1.14, 1.15, 1.16, 623/1.17, 1.18, 1.19, 1.2, 1.21, 1.22; 606/108, 606/151, 153, 154, 155, 156
See application file for complete search history.

(56) References Cited

U.S. PATENT DOCUMENTS 5,064,435 A * 11/1991 Porter .......................... 623/23.7
5,667,523 A 9/1997 Bynon et al. .................. 606/198

(Continued)

FOREIGN PATENT DOCUMENTS

WO WO 98/26731 A2 6/1998
WO WO 2004/017867 A1 3/2004

(Continued)

OTHER PUBLICATIONS

International Search Report and Written Opinion of the International Searching Authority for International Application No. PCT/US2009/000869, dated Jun. 19, 2009.

(Continued)

*Primary Examiner* — Ryan Severson
*Assistant Examiner* — Jonathan W Miles
(74) *Attorney, Agent, or Firm* — Brinks Hofer Gilson & Lione

(57) ABSTRACT

A coupling device is formed of a double tubing of a substantially non-porous membrane material, typically a conventional graft material, that is of inner and outer layers of membrane material. The inner and outer layers are coupled by bridging rings which allow the layers to be spaced from one another in use. Attached to the inner and outer layers are first and second stents. The stent is located on the inside of the double tubing, while the stent is located on the outside of the double tubing. The device can expand in effect to 'bulge' and thus to fill the gaps to the vessel wall and to the stent-graft sections. The device can provide reliable coupling of stent-grafts in vessels of varying diameter or in vessels inflicted with one or more aneurysms.

17 Claims, 2 Drawing Sheets

U.S. PATENT DOCUMENTS

| | | | |
|---|---|---|---|
| 5,735,892 A * | 4/1998 | Myers et al. | 623/1.13 |
| 5,769,884 A | 6/1998 | Solovay | 623/1 |
| 5,810,870 A | 9/1998 | Myers et al. | 606/198 |
| 6,475,232 B1 * | 11/2002 | Babbs et al. | 623/1.13 |
| 6,911,042 B2 | 6/2005 | Weadock | 623/1.23 |
| 7,166,124 B2 | 1/2007 | Xie et al. | 623/1.13 |
| 7,914,567 B2 * | 3/2011 | Pavcnik et al. | 623/1.13 |
| 8,257,430 B2 | 9/2012 | Mead | 623/1.35 |
| 2004/0098097 A1 | 5/2004 | Fogarty et al. | 623/1.13 |
| 2004/0176833 A1 * | 9/2004 | Pavcnik et al. | 623/1.13 |
| 2007/0010874 A1 | 1/2007 | Sun | 623/1.35 |
| 2007/0118208 A1 | 5/2007 | Kerr | 623/1.13 |
| 2007/0191930 A1 | 8/2007 | Lucas et al. | 623/1.36 |

FOREIGN PATENT DOCUMENTS

| | | |
|---|---|---|
| WO | WO 2004/047687 A1 | 6/2004 |
| WO | WO 2006/113501 A1 | 10/2006 |
| WO | WO 2007/053592 A2 | 5/2007 |

OTHER PUBLICATIONS

International Preliminary Report on Patentability for International Application No. PCT/US2009/000869, dated May 7, 2010.

* cited by examiner

PROSTHESIS COUPLING DEVICE AND METHOD

This application is a divisional application of U.S. application Ser. No. 12/867,101 filed on Oct. 21, 2001, which is a nationalization of PCT application PCT/US2009/000869 filed on Feb. 11, 2009, and claims the benefit of the filing date under 35 U.S.C. §119(e) of U.S. Provisional Patent Application Ser. No. 61/065,333 filed Feb. 11, 2008, the complete disclosures of which are incorporated herein by reference in their entireties.

TECHNICAL FIELD

The present invention relates to a prosthesis coupling device, to a prosthetic assembly and to a method of making a coupling device.

BACKGROUND ART

Prostheses for the repair of vascular defects, including for example vascular aneurysms, are well known in the art. A common prosthesis for treatment of such a medical condition is a stent graft. It is also known to provide such prostheses in modular form, for example when it is necessary for the prosthesis to straddle a plurality of vessels, such as the superior mesenteric artery and the iliac arteries. Similarly, a modular prosthesis may be provided in cases where the dimensions of the artery or other vessel to be treated would vary substantially from one end of the prosthesis to the other. Yet another example is where a medical condition necessitates the use of different types of prosthesis along the length of the site to be treated.

It is common for such modular prostheses to be coupled together by nesting one section within the other and expanding the innermost section against the interior surface of the outer section. Such expansion can be effected, for example, by means of a self-expanding element such as a self-expanding stent, or by a separate expansion mechanism, such as an expandable balloon. It will be apparent that in order to obtain a fluid-tight seal between the various modules of such a prosthesis the sections must have complementary dimensions at their point of coupling. This necessitates careful manufacturing and imposes consequential limitations on the design of the modules.

Furthermore, it is necessary in many medical treatments, such as in the treatment of aneurysms, the bypass of occluded or otherwise damaged vessels and so on, to provide a fluid-tight seal between the ends of the prosthesis and the walls of the vessel in order to avoid blood loss. This requires the prosthesis, for example the stent-graft, to be of a suitable dimension for the particular vessel being treated. As a result of this, a surgeon must select a suitable prosthesis size for the dimensions of the vessel as well as for the particular vessel characteristics at the place of implantation of the prosthesis. Particular problems can arise in the case of aneurisms, for example, where the vessel is enlarged at the ends of the prosthesis or at the point of coupling of two modules of a modular prosthesis.

DISCLOSURE OF THE INVENTION

The present invention seeks to provide a coupling device for a prosthesis and an improved prosthetic assembly.

According to an aspect of the present invention, there is provided a coupling device for a prosthesis including inner and outer coupling elements arranged concentrically one within the other and able to be spaced apart in the course of coupling; and a substantially non-porous membrane associated with at least the outer coupling element; wherein the outer coupling element is of a self-expandable form.

The coupling device is such that the outer coupling element can expand to abutment with the interior surface of a vessel wall into which the device is placed and, in conjunction with the membrane, can provide a substantially fluid-tight seal against the vessel wall. The inner coupling element provides a connection location for connecting together two modules of a prosthesis or other implant which, in the preferred embodiment, is not dependent upon the dimensions of the vessel in the location at which the device is fitted.

The inner coupling element is preferably also of a self-expandable type although this is not essential as the inner coupling element could be expandable by a separate expansion mechanism such as a balloon.

Where the inner coupling element is self-expandable, this is preferably of a size relative to the prosthesis to press there against, in other words of a natural, unbiased, diameter smaller than the outer diameter of the prosthesis to be coupled thereto.

In the preferred embodiment, the inner and outer coupling elements are stents. Advantageously, the membrane is of a known graft material.

It is preferred that the membrane forms part of the coupling device, although this is not essential. It is envisaged in some embodiments that the membrane could be a separate component, for example as a part of a graft of one of the modules to be connected by the coupling element.

Advantageously, the device includes a membrane associated with both the inner and outer coupling elements and most preferably the membrane is connected to both of the inner and outer coupling members. In this latter case, the membrane may be in the shape of a double concentric tube connected at either end, the inner and outer coupling elements being located, respectively, on the inner and outer tube layers.

Advantageously, the membrane is a unitary structure formed of first and second tubular portions in which the first tubular portion has a larger diameter than the second tubular portion and includes a tapering connecting piece between the first and second tubular portions, the second tubular portion being evertable or everted into the first tubular portion so as to provide the double concentric tube.

It will be appreciated that it will not be necessary in all cases to have both of the outer and inner coupling elements connected to a membrane as a fluid-tight coupling could be provided by a membrane covering only the outer coupling element, for example in cases in which the prosthetic sections to be coupled together themselves provide for a fluid-tight coupling at the side of the inner coupling element. This might also apply in cases in which the coupling element is provided over a single prosthetic module, for instances in applications in which the coupling is used in the fitting of a prosthetic element in a vessel of inner diameter larger than the outer diameter of the prosthesis.

It is preferred that at least the outer coupling element is located on an exterior surface of the membrane, although this is not essential.

According to another aspect of the present invention, there is provided a prosthesis including a coupling device as specified herein.

According to another aspect of the present invention, there is provided a method of forming a coupling device as specified herein, including the steps of providing a membrane of unitary structure formed of first and second tubular portions in which the first tubular portion has a larger diameter than the second tubular portion and a connecting piece between the first and second tubular portions; the method including the steps of connecting to the first and second tubular portions first and second coupling elements, everting the second tubular portion into the first tubular portion so as to provide the double concentric tube with first and second coupling elements located concentrically thereon.

The connecting piece may be sutured, welded or adhered to the outer tubular portion. In a preferred embodiment, the connecting piece has a frusto-conical shape.

It will be appreciated that the term concentric used herein is not intended to be limited to elements exactly superimposed on one another. It is envisaged, for example, that the first and second coupling elements could be of different longitudinal dimensions and/or could be longitudinally offset relative to one another. The term concentric is therefore intended to include arrangements in which the inner and outer connecting elements at least partially overlap concentrically.

The preferred embodiments provide a coupling element which has a degree of adjustability in the radial direction, in that the outer connecting element can expand outwardly to abut a vessel wall, while the inner connecting element extends inwardly thereof to couple to one or more prosthetic elements or modules. Thus, it is not necessary to size the prosthetic module precisely to the dimensions of the vessel, it being possible to chose a prosthetic element of smaller diameter than the vessel and still achieve, through the coupling device, a fluid-tight seal. In practice, the space between the inner and outer coupling elements will be filled with vascular fluid, aiding in the sealing on the coupling and prosthesis to the vessel.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
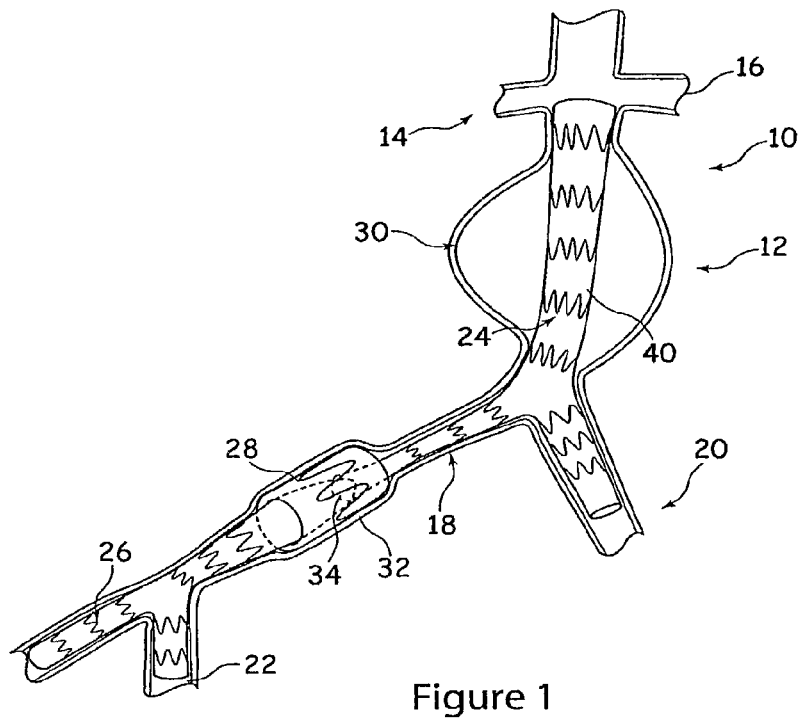
FIG. 1 shows an example of use of an embodiment of coupling device for connecting together modules of a branched stent-graft located within the superior mesenteric and iliac arteries.

Referring to FIG. 1, there is shown a double branched stent-graft 10 located within the superior mesenteric artery 12, just below the renal arteries 14, 16, and branching into the common iliac arteries 18 and 20. The stent graft 10 branches a second time, into the femoral artery 22.

For this purpose, the stent graft 10 is formed as two modules 24, 26 which are coupled to one another by an embodiment of coupling device 28 of the type taught herein and described in further detail below.

In this instance, an aneurysm 30 is located in the superior mesenteric artery 12, which has been isolated by the upper body portion 40 of the stent-graft 10, as well as a smaller aneurysm 32 in the iliac artery 18, at the location of the connection 34 between the two stent-graft modules 24, 26.

A conventional modular stent-graft 10 would couple the two modules 24, 26 by overlapping these and causing the inner-most section to expand against the outer section. For this purpose, the stent-graft sections of the modules 24, 26 would be conventionally sized to achieve a reliable and fluid-tight connection with one another.

As will be apparent from the example of FIG. 1, a conventional coupling between the stent-graft modules 24, 26 would not provide a fluid-tight seal around the connection zone as a result of expansion of the artery 18 due to the local aneurysm.

The teachings herein provide for a different coupling between the stent-graft modules 24, 26. FIG. 1 shows the preferred embodiment of coupling device 28 in situ. As can be seen, the coupling device 28 fills the space between the stent-graft sections of the modules 24, 26 and the vessel wall so as to provide for a fluid-tight coupling with the vessel wall, as well as a fluid-tight coupling between the stent-graft sections of the modules 24, 26. This is possible due to the radial volume achievable by the coupling by its ability to expand outwardly towards the vessel yet to retain a narrower inner diameter for the modules 24, 26.

As will become apparent from the description which follows, the coupling device 28 is able to expand to accommodate different sizes of vessel as well as different sizes of modules 24, 26. This property gives it also an adaptability lacking in existing prosthetic devices of this nature.

Figure 2:
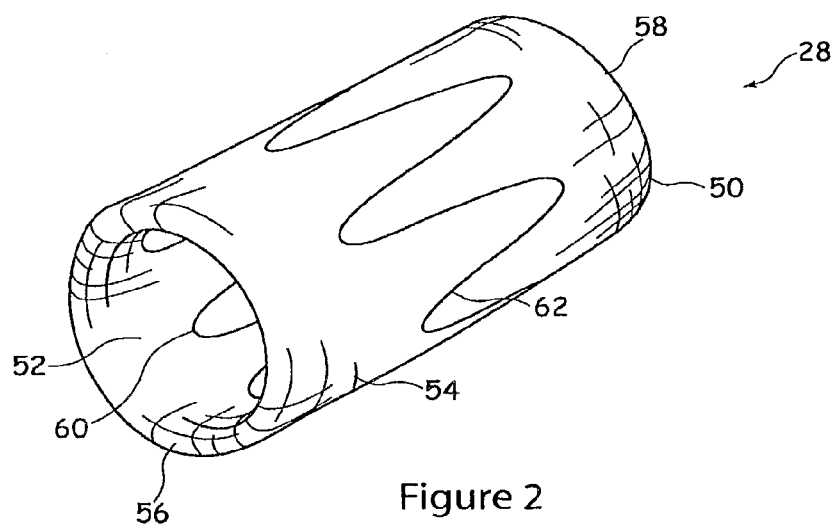
FIG. 2 is a perspective view of the preferred embodiment of coupling device.

Referring now to FIG. 2, there is shown in better detail the embodiment of coupling device 28 shown in FIG. 1. The device 28 is formed of a double tubing 50 of a substantially non-porous membrane material, typically a conventional graft material, providing inner and outer layers of membrane material 52 and 54 respectively. The inner and outer layers 52, 54 are coupled by bridging rings 56, 58 which allow the layers 52, 54 to be spaced from one another in use.

Attached to the inner and outer layers 52, 54 are first and second stents 60, 62 respectively. In this embodiment, the stent 60 is located on the inside of the double tubing, connected thus to the inner side of the inner layer 52. On the other hand, the stent 62 is located on the outside of the double tubing 50, connected thus to outer side of the outer layer 54. In this manner, the inner surfaces of the double tubing 50, which connect with the stent-graft modules, are free of surface stents, which can facilitate the creation of a fluid-tight seal between the stent-graft modules 24, 26 and the coupling device 28. The stents may be both self-expanding but this is not necessary. The stents may be of Ntitinol.

It is not necessary for the stents to be located on any particular surface of the tubings 60, 62 and they may, for example, both be on outside surfaces or both on internal surfaces of the tube layers. The choice will be dependent upon preference.

FIG. 2 shows the double tubing 50 provided with a single stent 60, 62 for each tubing layer 52, 54, located substantially at the centre of each layer. This allows the outer layer 54 to expand outwardly and the inner layer 52 to contract inwardly, so as to cause the tubing in effect to "bulge" and thus to fill the gaps to the vessel wall and to the stent-graft sections 24, 26. In some embodiments, there could be provided more extensive stenting of the tubular layers 52, 54, for example by provision of a plurality of stents per layer, extending for a greater proportion and in some instances substantially for the entire length of the tube layers 52, 54. Additional stenting can provide more even expansion/contraction along the length of the connector 28. If necessary, the bridging rings 56,58 could be made wider to accommodate greater bulging of the connector 28 or could be expandable, for example by being folded in concertina manner.

The stent 62 and outer tube layer 54 are of dimensions such that they can fit within a vessel 18 and expand to the vessel wall, including in the location of an aneurysm 32, so as to abut thereto in a fluid-tight manner. The stent 60 and inner tubing layer 52 are of dimensions that they can remain relatively contracted, or expand radially inwardly, so as to abut in fluid-tight manner, the stent-graft sections of the prosthetic modules 24, 26.

Figure 3:
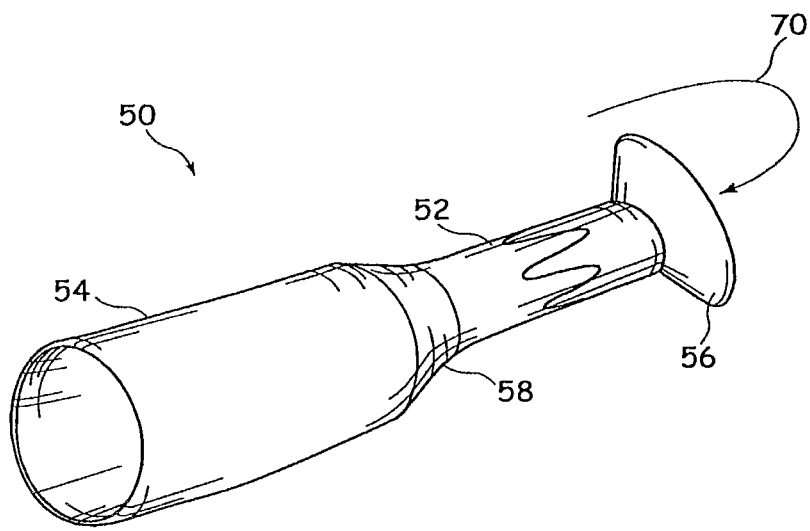
FIG. 3 is a perspective view of the connecting device of FIG. 2 during manufacture thereof.
Figure 4:
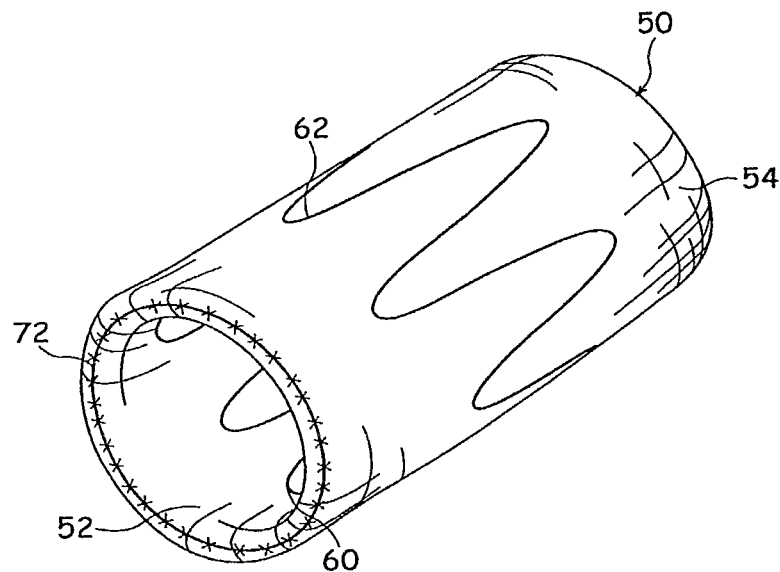
FIG. 4 is an enlarged view of the device of FIG. 3 in the final step of manufacture.

Referring now to FIG. 3, there is shown an embodiment of a preferred method of manufacturing the coupling device 28.

In this embodiment, the tubular element 50 is formed as a unitary structure of graft-like material having at one end the outer tubular layer 54 and at the other end the inner tubular layer 52. Coupling the outer and inner layers 54, 52 is a frusto-conical section forming the bridge 58. At the other end of the inner tubular layer 52 there is provided a flared portion forming, after manufacture, the bridging element 56.

The stents 60, 62 are then fitted to the tubular elements 52, 54, by stitching or by any other method known in the art or otherwise suitable for the purpose.

After fitting of the stents 60, 62, the narrower end of the structure 50, that is the inner tubular layer end, is everted, in the direction of the arrow 70 in FIG. 3 and in so doing drawn into the outer tubular layer 54. The step of eversion brings the outer and inner layers 52, 54 into a coaxial arrangement, with the flared end exiting beyond the free end of the outer tubular layer 54. The flared end 56 can then be stitched by suitable sutures 72 to complete the structure. The location of the suture line 72 is not critical and can be chosen to be at any preferred location at the end of the structure 50 or around the inner or outer layers 52, 54 by suitable choice of the respective lengths of the material forming the flange 56 and wider portion 54.

The completed coupling device 10 is such that the inner and outer layers 52, 54 can expand in different ways, as indicated above, as they are in practice substantially independent of one another. The structure can therefore be made to "bulge", that is such that the outer layer 54 expands outwardly while the inner layer 52 contracts inwardly or retains a smaller diameter.

In one particular example, the coupling device 28 has an outer diameter of 16 mm and an inner diameter of 9-10 mm. The dimensions will be dependent upon the particular medical application.

In practice, when in situ, the coupling device 28 will fill with vascular fluid, that is in the chamber formed between the inner and outer layers 52, 54, as a result of the slightly porous nature of the membrane forming the tubular element 50. This has the benefit of assisting the seal against fluid flow around the coupling device 28, that is between the vessel wall and the outer layer 54 of the tubular structure 50.

The device is advantageously fitted first into a patient's vasculature, in the example of FIG. 1 at the location of the aneurysm 32 in the iliac artery 18, and allowed to expand such that the outer tubular layer 54 abuts and is held against the vessel wall. The stent-graft 10 is then fitted, typically by first fitting the upper module 24 and then the lower module 26. The respective branches of the modules 24, 26 are located within the coupling device 28 and then expanded to abut against and connect to the inner tubular layer 52, so as to be coupled substantially in fluid-tight manner thereby.

Fixing elements of known form, such as barbs may be provided on the stent-graft sections and/or on the coupling device 28 in order to secure the connection, although in many cases this would not be necessary.

The coupling device could also be used in other applications. One example is for use in healthy vessels having a larger diameter than a stent-graft or other prosthesis to be fitted in the vessel, another is for application in a vessel having a reducing diameter along the length thereof to be fitted with such a prosthesis. In the latter example, the coupling device could usefully be located at an area in the vessel having a wider diameter, thus allowing the use of a stent-graft, for example, of diameter smaller than the wider part of the vessel.

Although the embodiment shown in FIGS. 1 to 4 provides a coupling device which is covered completely with a membrane 50, this is not essential in all applications. For example, it is envisaged that in some applications the membrane might not extend fully into the inner layer 52, for example to leave the stent 60 thereof partially exposed. In such an event, it is envisaged that the modules 24, 26 coupled by the device 28 would provide the required inner seal.

It is also envisaged that the membrane need not be an integral part of the coupling device 28. For example, it is possible for the coupling device 28 to be formed as a double layered flexible framework with inner and outer stent sections 60, 62 and for the device to make use of a graft material provided at one end, for example, of one of the modules to be connected by the coupling element 28.

We claim:

1. A prosthesis comprising:
   an outer expandable element having an inner surface;
   an inner expandable element concentrically disposed within the outer expandable element, and having an outer surface;
   the outer expandable element having an expanded diameter;
   the inner expandable element having an expanded diameter less than first diameter;
   at least one bridging member connecting the inner and outer expandable elements;
   wherein, in the expanded diameters, the outer expandable element expands radially outward away from the inner expandable element, such that the inner surface and the outer surface are not in contact.

2. The prosthesis of claim 1, wherein the bridging member comprises graft material.

3. The prosthesis of claim 2, wherein the bridging member comprises a tube of graft material having an inner surface and an outer surface.

4. The prosthesis of claim 3, wherein the outer expandable element is disposed on the outer surface of the tubular graft material and the inner expandable element is disposed on the inner surface of the graft material.

5. The prosthesis of claim 1, wherein in the expanded diameters an annular space is defined between the outer expandable element and the inner expandable element.

6. The prosthesis of claim 5, wherein the tubular graft material comprises two concentric layers of graft material.

7. A prosthesis comprising:
   an outer tubular coupling element and an inner tubular coupling element arranged at least partially concentrically within the outer tubular coupling element, each coupling element having an expanded configuration and a contracted configuration;
   where the inner coupling element and the outer coupling element are radially spaced from one another by a first distance in the contracted configuration and by a second distance in the expanded configuration, and where the second distance is greater than the first distance.

8. A device according to claim 7 where at least one of the outer coupling element and the inner coupling element is self-expandable.

9. A device according to claim 7 where each of the outer coupling element and the inner coupling element is self-expandable.

10. The device of claim 7 where either or both of the outer coupling element and the inner coupling element comprise one or more stents.

11. The device of claim 7 further comprising membrane connecting the inner and outer coupling elements.

12. The device of claim 11, wherein the membrane comprises tubular graft material.

13. The device of claim 12, wherein the tubular graft material comprises two concentric layers of graft material.

14. The device of claim 7 where, in the expanded configuration, the inner coupling element has a diameter that is about 60% the diameter of the outer coupling element.

15. A prosthesis comprising:
an expandable tubular structure comprising an outer stent graft portion and an inner stent graft portion arranged at least partially concentrically within the outer stent graft portion, the tubular structure comprising a contracted configuration and an expanded configuration;
where the outer stent graft portion expands outwardly substantially independently of the inner stent graft portion such that in the expanded configuration, the inner stent graft portion is radially inwardly spaced away from the outer stent graft portion.

16. The device of claim 15 wherein, in the expanded configuration, the tubular structure has an inner diameter that is about 60% the diameter of the outer coupling element.

17. The device of claim 15 wherein the inner stent graft portion and the outer stent graft portion each comprise tubular stent graft portions.

* * * * *